United States Patent [19]

Fanta et al.

[11] Patent Number: 4,845,035

[45] Date of Patent: Jul. 4, 1989

[54] ENZYME IMMOBILIZATION WITH A HYDROLYZED POLYSACCHARIDE GRAFT COPOLYMER

[75] Inventors: George Fanta, Peoria; Patricia J. Slininger, Metamora, both of Ill.

[73] Assignee: The United States of America as represented by the Secretary of Agriculture, Washington, D.C.

[21] Appl. No.: 104,899

[22] Filed: Oct. 6, 1987

[51] Int. Cl.$^4$ .................... C12N 11/10; C12N 11/12; C12N 11/08; C12P 19/20

[52] U.S. Cl. .................................. 435/178; 435/95; 435/96; 435/99; 435/105; 435/179; 435/180

[58] Field of Search ............... 435/174, 177, 178, 179, 435/180, 182, 96, 95, 99, 104, 105; 524/48

[56] References Cited

U.S. PATENT DOCUMENTS

| | | | |
|---|---|---|---|
| 3,985,616 | 10/1976 | Weaver et al. | 435/178 |
| 4,038,140 | 7/1977 | Jamorek et al. | 435/178 |
| 4,134,863 | 1/1979 | Fanta et al. | 435/178 X |
| 4,194,998 | 3/1980 | Fanta et al. | 435/178 X |
| 4,338,401 | 7/1982 | Gemonesé435 | 178/ |
| 4,483,950 | 11/1984 | Fanta et al. | 524/48 |
| 4,663,163 | 5/1987 | Hou et al. | 435/178 X |

OTHER PUBLICATIONS

O. R. Zaborsky, *Immobilized Enzymes*, CRC Press, Cleveland, Ohio, 175 pages (1973).

P. J. Reilly, "Starch Hydrolysis with Soluble and Immobilized Glucoamylase," In: *Applied Biochemistry and Bioengineering 2:* 185–207, Academic Press, Inc. (1979).

D. D. Lee, G. K. Lee, P. J. Reilly, and Y. Y. Lee, "Effect of Pore Diffusion Limitation on Dextrin Hydrolysis by Immobilized Glucoamylase," *Biotechnology and Bioengineering 22:* 1–17 (1980).

H. H. Weetall, "Applications of Immobilized Enzymes," *Immobilized Enzymes for Industrial Reactors,* Ed. R. A. Messing, Academic Press, New York, Chapter 10, pp. 207–212 (1975).

D. D. Lee, Y. Y. Lee, P. J. Reilly, E. V. Collins, and G. T. Tsao, "Pilot Plant Production of Glucose with Glucoamylase Immobilized to Porous Silica," *Biotechnology and Bioengineering 18:* 253–267 (1976).

J. Kobarzewski and A. Paszczynski, "Catalytic Properties of Immobilized Crude and Pure Glucoamylase from *Aspirgillus niger C.*," *Biotechnology and Bioengineering 25:* 3207–3212 (1983).

G. F. Fanta and W. M. Doane, "Grafted Starches," In: *Modified Starches: Properties and Uses,* Ed. O. B. Wurzburg, CRC Press, Inc., Chapter 10, pp. 149–178 (1986).

*Primary Examiner*—David M. Naff
*Attorney, Agent, or Firm*—M. Howard Silverstein; John D. Fado; Margaret A. Connor

[57] ABSTRACT

Immobilized enzyme-polysaccharide graft copolymer products are prepared by hydrolyzing a polysaccharide graft copolymer and then contacting the hydrolyzed copolymer with an enzyme to immobilize the enzyme on the copolymer. The copolymer-enzyme products retain large quantities of active enzyme, and activity of the enzyme is retained over long periods of use. In the case of glucoamylase immobilized in accordance with the method of the invention, improved yield of glucose from starch is obtained.

14 Claims, 1 Drawing Sheet

ENZYME IMMOBILIZATION WITH A HYDROLYZED POLYSACCHARIDE GRAFT COPOLYMER

BACKGROUND OF THE INVENTION

1. Field of the Invention

This invention relates to and has among its objects the provision of novel polysaccharide graft copolymer-enzyme products and methods for preparing them.

2. Description of the Art

Enzyme immobilization provides many important advantages over use of enzymes in soluble form, namely, enzyme reuseability, continuous operation, controlled product formation, and simplified and efficient processing. Continuous reactors utilizing immobilized enzymes provide high productivities and yields, and minimize downtime, enzyme costs, fermentor size, and capitol investment.

Conventional methods for immobilization of an enzyme on a solid substrate include covalent attachment of the enzyme to organic or inorganic carriers using cross linking agents such as glutaraldehyde; entrapment of the enzyme in a polymerizing polymer, and adsorption onto insoluble substrates such as ion exchange resins, activated charcoal, alumina, and the like. (For a detailed discussion, see *Immobilized Enzymes* by O. Zaborsky, CRC Press, 175 pages, 1973.)

Glucoamylase is one of the most important industrial enzymes. In the food and beverage industries, glucoamylase has been an important enzyme for starch saccharification because it can achieve complete breakdown of starch to glucose. In order to make the enzyme continuously reuseable, workers have immobilized it on various substrates but have encountered low enzyme activities, gradual deactivation of the enzyme, and low glucose yields (P. J. Reilly in *Applied Biochemistry and Bioengineering* 2: 185–207, Academic Press, Inc. (1979)). One of the reasons is the effect of slow diffusion of glucoamylase into the pores of the carrier substrate. Slow diffusion can affect not only the overall rate of hydrolysis but also the concentrations of intermediates as the reaction sequence proceeds (Lee et al., *Biotechnology and Bioengineering* 22: 1–17 (1980)). Low product yields can occur if high molecular weight starch fractions are excluded from small pores or if glucose, being slow to diffuse out of pores, forms reversion products such as maltose, isomaltose, and maltotriose. Further, temperature extremes arising from inadequate heat exchange are known to speed enzyme deactivation, especially in packed bed reactors.

H. Weetall in *Immobilized Enzymes for Industrial Reactors*, Ed., R. A. Messing, Academic Press, New York, pp. 207–212 (1975); Lee et al., 1980, supra, and Lee et al., *Biotechnology and Bioengineering* 18: 253–267 (1976) have indicated that many of these problems can be bypassed if reaction temperature is sufficiently low to maintain enzyme stability and if support diameter is sufficiently small to eliminate diffusion effects. Pilot scale operation, approximating these conditions, has shown promise for glucoamylase linked via glutaraldehyde to alkylamine porous silica (Lee et al., 1976, supra). Although glucoamylase activity was infinitely stable at the 38° C. operating temperature, the reaction still showed evidence of diffusion limitation, and small yield losses of 1.5% glucose concentration were noted even though the catalyst particles were 300–600 μm in diameter. While immobilization of glucoamylase by adsorption of the enzyme onto substrates such as ion exchange resins, DEAE-cellulose, CM-cellulose, CM-sephadex, and the like (Zaborsky, supra, pp. 80–81) is known, it is impossible to predict what substrates will bind and retain significant quantities of active glucoamylase and provide good product yield because adsorption of enzymes onto water-insoluble matrices depends on (1) the specific natures of both carrier substrate and enzyme and (2) is attributed to various mechanisms, e.g., ion exchange, physical adsorption, hydrophobic interactions (physicochemical bonding), van der Waals attractive forces, etc.

SUMMARY OF THE INVENTION

We have now surprisingly discovered novel polysaccharide graft copolymer-enzyme products. The novel products are prepared by hydrolyzing a polysaccharide graft copolymer to remove a portion of the polysaccharide backbone and then contacting the hydrolyzed copolymer with an enzyme to immobilize the enzyme on the copolymer matrix.

Surprisingly, by this procedure polymer-enzyme products are obtained wherein large quantities of active enzyme are retained and wherein activity of the enzyme is retained over long periods of use. By use of the method of the invention, hydrophobic polymers are amenable to penetration and adsorption of aqueous enzyme thereby resulting in stable polymer-enzyme products without the use of chemical binding agents. In the case of glucoamylase immobilized in accordance with our method, improved glucose yield is obtained. Further, glucoamylase activity is as high or higher than glucoamylase linked to a carrier substrate via glutaraldehyde.

In accordance with this discovery, it is an object of the invention to provide methods for preparing hydrolyzed polysaccharide graft copolymer-enzyme products wherein active enzyme is immobilized onto a hydrolyzed polysaccharide graft copolymer matrix.

A further object of the invention is to obtain reusable, stable, active immobilized enzyme products without the additional processing step and inherent cost of use of a crosslinking agent.

Another object of the invention is the provision of simple, cost-saving, efficient methods to obtain immobilized enzymes.

Other objects and advantages of the invention will become readily apparent from the ensuing description.

DETAILED DESCRIPTION OF THE INVENTION

Figure 1:
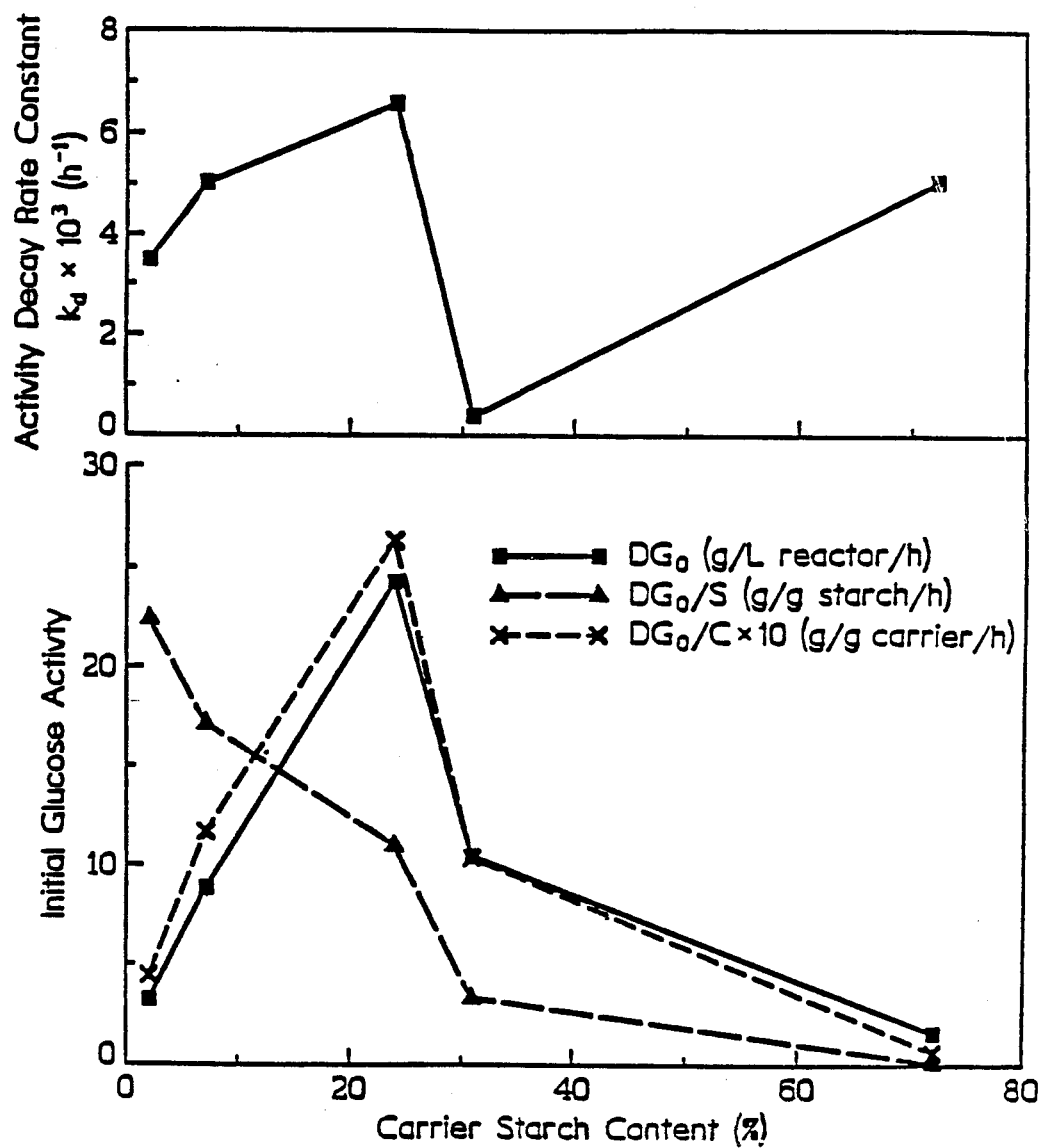
FIG. 1 shows glucose productivity and enzyme activity decay rate for glucoamylase immobilized on acid-hydrolyzed starch graft polyacrylonitrile as a function of graft copolymer starch content.

To prepare the polymer-enzyme products of the invention, a polysaccharide graft copolymer is hydrolyzed to remove a portion of the polysaccharide backbone; next, the hydrolyzed polysaccharide graft copolymer is contacted with an aqueous enzyme to immobilize the enzyme on the copolymer matrix.

Procedures for the preparation of polysaccharide graft copolymers are well known. A detailed description is given in *Modified Starches: Properties and Uses*, Ed. O. B. Wurzburg, Chapter 10, 'Grafted Starches' by G. F. Fanta and W. M. Doane, CRC Press, Inc. (1986), which is hereby incorporated by reference. Briefly stated, polysaccharide graft copolymers are prepared by first generating free radicals on the polysaccharide backbone, for example, by reacting the polysaccharide with a very strong oxidizing agent such as ceric ion or by irradiating the polysaccharide, and then allowing these free radicals to initiate the polymerization of a monomer. The resulting polysaccharide graft copolymer has a polysaccharide backbone with high molecular weight polymer grafts on the polysaccharide.

Polysaccharides useful as starting materials include all types of starches, both granular and gelatinized, for example rice, potato, corn, wheat, and the like; hydrolyzed starch, for example, dextrin, maltodextrin, and carbohydrates such as cellulose, and xylan. An exemplary polysaccharide is corn starch because of its low cost and apparent superior performance.

Monomers useful in preparing the polysaccharide graft copolymers are vinyl or acrylic monomers yielding water-insoluble polymers. Examples of such polymers are polyacrylonitrile (PAN), poly(methyl acrylate), poly(methyl methacrylate), poly(ethyl acrylate), poly(butyl acrylate), polystyrene, and the like.

The vinyl or acrylic polymer content (% add-on) of the polysaccharide graft copolymer should be about 1-60% weight percent and preferably 30% or less.

Hydrolysis of the polysaccharide graft copolymers is carried out by any method known in the art, for example, chemical hydrolysis, such as treatment with an acid such as hydrochloric acid; with periodate-alkali; with perchloric acid in acetic acid; or with trifluoroacetic acid, or by enzymatic hydrolysis, for example, α-amylase. Hydrolysis is carried out so that the polysaccharide content of the polysaccharide graft copolymer after hydrolysis is 2 to 70%, preferably 15 to 40%. The preferred granule size of the hydrolyzed polysaccharide graft copolymer is 3 to 110 microns. Factors which affect hydrolysis and thereby final polysaccharide content include temperature, type and concentration of the hydrolyzing agent, and reaction time. As known in the art and as illustrated in the Examples below, optimum conditions to achieve a hydrolyzed polysaccharide graft copolymer with a desired polysaccharide content can be readily determined by routine test runs.

To form the polymer-enzyme products of the invention, the hydrolyzed polysaccharide graft copolymer is contacted with an aqueous solution of an enzyme for a time sufficient to allow the enzyme to penetrate and bind to the polymer. Generally, about 4 parts to 1 part by weight of enzyme per part of hydrolyzed graft copolymer are used. The mixture is gently agitated by conventional means such as shaking, stirring, or the like, while being held for 5 to 30 minutes at a temperature of about 10°-35° C. The polymer-enzyme product is separated from the mixture by any technique known to those in the art, for example, by filtration, and is washed with water to remove excess reagents.

Surprisingly, hydrolysis of the polysaccharide backbone causes the hydrophobic polymeric matrix to have a structure and morphology (three-dimensional orientation of polymer strands) amenable to penetration and binding of the enzyme without the need of a chemical binding agent, and products are obtained wherein large quantities of active enzyme are retained and where activity of the enzyme is retained over long periods of use. It is theorized that immobilization of the enzyme is due to such mechanisms as adsorption, hydrogen bonding, ionic effects, or a combination thereof. In addition, it appears that affinity of the enzyme to the polysaccharide in the copolymer after hydrolysis plays a role in immobilization. Thus the preferred enzymes used to prepare the polymer-enzyme products are those having an affinity for polysaccharides, for example, polysaccharide-degrading enzymes such as α- or β-amylase, glucoamylase, cellulase, and xylanase.

The hydrolysis and enzyme contacting steps can be carried out separately as illustrated in Example 1 below. Alternately, these steps may be carried out at the same time, as described in Example 2, below, where an enzyme is both the hydrolyzing agent and the enzyme to be immobilized.

The starting enzyme to be immobilized is in aqueous solution. When necessary the pH of the solution is adjusted by conventional methods such as adding an acid, buffer, etc., to a level at which the enzyme is active. Appropriate pH's to use with any particular enzyme are described in the literature. In many cases a pH of about 3 to 7 is employed. It may further be noted that oftentimes the starting material already contains a buffer or other pH adjusting agent so that when it is mixed with water the resulting dispersion will exhibit a pH at which the enzyme is most soluble. This is particularly the case with commercially available enzyme preparations.

The products of the invention can be utilized in a variety of ways. Important uses include hydrolyzing starch to glucose, maltose, and oligosaccharides; hydrolyzing cellulose to glucose, and hydrolyzing xylan to xylose.

EXAMPLES

The following examples are intended only to further illustrate the invention and are not intended to limit the scope of the invention which is defined by the claims.

EXAMPLE 1

Hydrolyzed polysaccharide graft copolymer-enzyme products were prepared, and their activity and stability were tested by monitoring their glucose productivity in a continuous reactor fed maltose.

Polysaccharide Sources for Copolymerization. Various starches and cellulose were used as starting materials for the graft copolymerizations. These polysaccharides had equilibrium moisture contents of 10-15%, as determined by vacuum drying at 100° C. over $P_2O_5$. All weights are on a dry basis.

Starches. Globe Pearl corn starch from CPC Internal was routinely used to prepare starch graft copolymers. However, rice (Sigma Chemical Co.) and potato (Boise Cascade Chemical Operations) starches were used to investigate effects of starch granule size. Large granules of potato starch were obtained by suspending starch in water and allowing it to partially settle. The upper layer containing suspended fines was then discarded. The collected starch fraction was resuspended and sedimented seven more times, and the final settled layer of large granule potato starch was separated by filtration and allowed to air dry.

Cellulose. Cellulose graft copolymer was prepared from bleached softwood pulp (Alberta Hi-Brite) from St. Regis Paper Co. Analyses showed its contents to be 0.06% lignin and 85.8% alpha-cellulose, the remainder being pentosans.

Graft Polymerizations. Starch-g-PAN. In a typical reaction, a stirred slurry of 20.0 g of starch in 400 mL of water was sparged with a slow stream of nitrogen for 1 hour at 25° C. Ten grams of acrylonitrile (Eastman Kodak Co.), previously distilled through a 14-inch Vigreuz column, was added followed by a solution of 0.676 g of ceric ammonium nitrate (Fisher Certified ACS Grade) in 6 mL of 1N nitric acid. Cerium (IV) initiates polymerization by generating free radicals on the starch backbone. The polymerization was allowed to proceed for 2 hours at 25°–29° C.; and the graft copolymer was then separated by filtration, washed with water, and air-dried. Equilibrium moisture content was determined by vacuum drying at 100° C. over $P_2O_5$, and weight percent PAN in the copolymer (% add-on) was estimated from weight gain. Larger batches starting with 200 g starch were prepared by using a 10-fold scale-up of the above quantities.

Starch-g-PAN copolymers were analyzed and characterized after removing small amounts of ungrafted PAN (in most cases less than 2% by weight) via extraction with dimethylformamide (DMF) at room temperature. The percent add-on was then more precisely determined from the weight loss due to starch removal from a preweighed sample of the DMF-extracted starch-g-PAN. Starch was removed via hydrolysis with 0.5N HCl under reflux for 90 minutes. Average molecular weight of the remaining grafted PAN could then be determined by measuring intrinsic viscosity in DMF solution at 25° C. Graft copolymers used in enzyme studies were normally not extracted with DMF. Preparation and characterization of starch-g-PAN copolymers are summarized in Table I.

Cellulose-g-PAN. Cellulose-g-PAN (27.2% PAN by weight gain) was prepared from 20.0 g of softwood pulp and 10.0 g of acrylonitrile in 800 mL of water. Extraction of a portion of the product with DMF removed 2.1% of its weight as ungrafted PAN, and degradation of the cellulose portion with sodium periodate-sodium methoxide showed that grafted PAN had an average molecular weight of 77,000.

Starch-g-poly(methyl methacrylate). Corn starch-g-poly(methyl-methacrylate) having 33.3% add-on by weight gain was prepared by the same method as numbers 91 and 34 of Table I except that methyl methacrylate (Eastman Kodak Co.), distilled through a 14-inch Vigreux column, replaced acrylonitrile. Ungrafted poly(methyl methacrylate) amounted to 5.4% of the product weight and was removed by extraction of the copolymer (moistened to a water content of 29%) with 1,2-dichloroethane. Percent add-on by weight loss upon acid hydrolysis was 27.8, and average molecular weight of grafted poly(methyl methacrylate) was 830,000, as calculated from the intrinsic viscosity in benzene at 30° C.

Starch-g-polystyrene. Corn starch-g-polystyrene (27% add-on by weight gain) was prepared by heating a semi-solid mixture of starch, styrene (Eastman, extracted with 5% NaOH and then with water), water, and potassium persulfate in a weight ratio of 100:50:25:1. Preparation of this polymer was as follows: To a paste prepared from 333 g (300 g, dry basis) of starch and 150 g of styrene was added a solution of 3.0 g of potassium persulfate in 75 mL of water, and the resulting mixture was thoroughly blended. Air was displaced by four evacuations (to 50 mm) followed by repressuring (to atmospheric pressure) with nitrogen, and the mixture was heated in an 80° C. oven for 3 hours. A temperature of 100° C. was reached during polymerization. The reaction mass was ground in a blender with ethanol to reduce particle size, and the polymer was washed with ethanol and dried.

Graft Copolymer Hydrolysis and Contacting with Glucoamylase. As standard procedure, 5.00 g of 28% add-on starch-g-PAN (not extracted with DMF) was suspended in 150 mL of 0.5N HCl and heated with stirring udner reflux for 90 minutes. After most of the starch was thus removed by hydrolysis, the remaining solid was removed by filtration, washed 4 times with water, and divided into halves. With one half set aside for further analysis, the other was suspended in 50 mL of pH 4 acetate buffer (0.1N). This was mixed with a second solution containing 25 mL buffer and 2.5 g glucoamylase ("Diazyme L-100," Miles Laboratories, Inc.). After the resulting mixture was stirred for 30 minutes at room temperature, the suspended solid (copolymer-enzyme complex) was separated by filtration and washed 5 times with water. Loosely-bound glucoamylase was further extracted by stirring the solid overnight at room temperature in 75 mL of 0.5N sodium chloride, filtering it, and washing it 4 times with water. The copolymer-enzyme complex was kept as a wet solid on the filter funnel until it was charged into the 100-mL reactor for evaluation (approximately 2 hours elapsed time). The characterization data for the starch-g-PAN copolymers are shown in Table I.

TABLE I

| | | | | DMF[a] Insoluble Fraction | | |
| --- | --- | --- | --- | --- | --- | --- |
| Number | Starch (g) | g AN | % Add-on, from wt. gain | % of Total Product | % Add-on, from wt. Loss | Average mol. wt. of PAN Grafts |
| 91 | Corn (20) | 10 | 28.8 | —[b] | —[b] | —[b] |
| 34 | Corn (20) | 10 | 28.1 | 98.8 | 28.2 | 19,600 |
| 50 | Corn (200) | 100 | 27.8 | 99.0 | 28.5 | 24,200 |
| 28 | Corn (20) | 30 | 56.0 | 88.0 | 50.7 | 86,000 |
| 33 | Corn (200) | 50 | 12.3 | 99.7 | 14.0 | 16,700 |
| 83 | Potato (20) | 10 | 26.1 | 99.6 | 22.5 | 32,600 |
| 89 | Rice (20) | 10 | 26.5 | 98.0 | 23.5 | 17,700 |

[a]Abbreviations: DMF = dimethylformamide; AN = acrylonitrile; PAN = polyacrylonitrile.
[b]Not determined.

PAN Samples Used for Comparison with Starch-g-PAN Samples.

PAN Homopolymer. A 0.70 g sample of PAN Type A (E. I. DuPont de Nemours and Co.) was wetted with ethanol, gently masticated to break up lumps, and let stand for 30 minutes. The polymer was transferred to a filter tunnel, washed fived times with water, and contacted with glucoamylase ("Diazyme L-100," Miles Laboratory, Inc.) according to the standard procedure.

PAN Homopolymer Precipitated from DMF or DMSO. Solutions of 0.70 g PAN Type A (E. I. Du Pont de Nemours and Co.) in 20 ml of DMF and in 20 ml of DMSO were prepared. PAN was precipitated by adding the solutions to 300 ml of water and stirring the resulting mixtures at high speed in a Waring blender.

Polymers were removed by filtration, washed five times with water and contacted with glucoamylase ("Diazyme L-100," Miles Laboratory, Inc.) as in the standard procedure.

Acid-Hydrolyzed Starch-g-PAN Precipitated from DMF. Starch-g-PAN with 28% add-on was hydrolyzed by heating under reflux for 90 minutes in 0.5N HCl. The washed and air-dried polymer granules were dissolved in DMF. The DMF solution was concentrated to a thick syrup and stirred at high speed (Waring blender) with excess water to precipitate the polymer. The polymer was separated by filtration, washed with water, and contacted with glucoamylase as in the standard procedure.

PAN Prepared by Glucose-Ce(IV) Initiation. The same procedure for synthesis of starch-g-PAN was followed except that glucose was used in place of starch. The PAN with glucose end groups was separated by filtration, washed three times with water, and stored as the wet solid. Conversion of monomer to polymer was 14%. A 0.7 g sample of water-wet PAN was acid refluxed, washed, and contacted with glucoamylase according to the standard procedure.

Test Procedure. The activity and stability of hydrolyzed polysaccharide graft copolymer-enzyme products were tested by monitoring their glucose productivity in a continuous reactor fed a solution of 30 g/L maltose in 0.1N acetate buffer. The reactor vessel was a 100-mL, jacketed Bellco spinner flask modified with extra ports to accomodate continuous flow operation. A homogeneous suspension was maintained throughout each run with a magnetic stirrer. Unless otherwise noted, the reactor was controlled at 50° C. by water circulation between a water bath and the jacket surrounding the reaction chamber and at pH 4 by the acetate-buffered feed. The polymer-enzyme product granules averaged about 15 microns in diameter. They were easily retained in the reactor by attaching to the effluent line a coarse porosity filter, such as Waters' stainless steel solvent filter (part 25531). The effluent pump speed was set to exceed that of the feed pump, and the holding volume in the reactor was set at 100 mL by positioning the effluent filter appropriately.

Freshly washed polymer-enzyme product was rinsed from the filter funnel to the reactor and suspended in the 100 mL holding volume ($V_R$) with feed solution. To determine initial enzyme activity, the reactor was allowed to run in a batch mode for 2 hours as samples were drawn for analysis. Based on activities calculated from the batch reaction, the feed rate to the reactor was set so that over 10 g/L maltose remained in the effluent in order to ensure that enzyme activity was rate limiting. On a daily basis, fresh effluent samples (approximately 5 mL) were collected and assayed for maltose and glucose (G) concentrations and for free glucoamylase activity. Volumetric flow rates (Q) were calculated based on effluent volumes collected over timed intervals (approximately 24 hours); dilution rate (D) equalled $Q/V_R$. The volumetric glucose productivity of the reactor was calculated as $QG/V_R$ with units of mass glucose/h/reactor volume. Specific productivities based on mass of carrier, polymer, e.g., PAN, and carrier polysaccharide were calculated as DG/C, DG/P, and DG/S, respectively.

Analyses.

Infared Spectra of Starch-g-PAN. Composition of hydrolyzed starch-PAN grafts was determined by fourier transform infrared analysis (Mattson Cygnus 25 FTIR) of solid samples in KBr discs. Three discs were prepared for each sample and five for the PAN standards. Spectra were averaged. Standard PAN, Type A, was refluxed for 30 min in 0.5N HCl, filtered, washed, and dried. A 3.6 g quantity of corn starch was heated to reflux temperature in 150 mL of 0.5N HCl, cooled immediately, and low molecular weight material was separated by dialysis against distilled water. The retentate was freeze-dried, and 1.5 g of hydrolyzed starch was recovered.

By dividing the absorbance of the unknown at 2243 cm$^{-1}$ by the absorbance of the PAN standard at this wavelength, a weight fraction of PAN in the unknown sample was determined. Subtracting the contribution of this amount of PAN to the unknown spectrum at 1028 cm$^{-1}$ and dividing the result by the starch standard absorbance at 1028 cm$^{-1}$ gave a weight fraction of starch in the unknown sample. Percent compositions was then calculated from the weight fractions of the two components. Results for hydrolyzed starch-PAN grafts agreed well with compositions calculated from weight loss on hydrolysis.

Maltose and Glucose. Maltotetrose, maltotriose, maltose, and glucose concentrations were determined on a Waters High Performance Liquid Chromatographic system equipped with a Biorad HPX-87H ion exclusion column and a refractive index detector. The column was operated at 28° C. with 0.0017N $H_2SO_4$ as the mobile phase. Retention times of maltotetrose, maltotriose, maltose, and glucose were 6.5, 7.2, 7.9 and 8.4 min, respectively.

Free Glucoamylase Activity. To evaluate leakage of enzyme from the carrier, samples of filtered effluent were incubated at 50° C. and monitored for continued degradation of maltose. Glucose and maltose concentrations were measured after 0, 24, and 48 hours.

Scanning Electron Microscopy. Freeze-dried solids were mounted on aluminum stubs with double-sided tape and were coated with a 200 angstrom layer of gold-palladium (60-40) alloy. Samples were then examined and photographed in a Hitachi ISI scanning electron microscope.

Enzyme Activity and Reactor Stability. Three batches of starch-g-PAN copolymer (Table I, #91, 34, 50) were prepared, hydrolyzed, treated with glucoamylase and then reacted with maltose fed at a 0.1 h$^{-1}$ dilution rate. Two additional runs were made in which faster dilution rates were used. It was found that acid hydrolysis (90 min reflux in 0.5N HCl) removed all but about 2% of the polysaccharide and yielded copolymer-enzyme granules having a size of about 5 to 26 microns. The activity of glucoamylase (mass of glucose produced per liter reactor volume per hour) immobilized on five similarly prepared batches of 28% add-on starch-g-PAN was measured over time in the continuous reactor. The data indicated that the enzyme was immobilized on the copolymer and that the decline in activity of the enzyme over time was independent of dilution rate. Further, free glucoamylase was not detected in the effluent stream. This indicates that the decline in enzyme activity was due to inactivation of the enzyme and not to loss of the enzyme from the copolymer. The gradual loss of glucose productivity was consistent with first-order enzyme deactivation kinetics. It should be noted that Lee et al., 1976, supra, found that silica-immobilized glucoamylase exhibited a first order decay rate. Based on chromatography data, there was no evidence of reversion products in any of the runs, and mass balances on the reactor indicated that glucose yields were essentially 100% of theoretical based on maltose consumed.

Variation of Enzyme Activity and Deactiviation Rate with Temperature. Tests showed that temperature influenced both the reaction and decay rates of starch-g-PAN immobilized glucoamylase. Like soluble glucoamylase, the reaction rate of the immobilized enzyme was optimum at 60° C. The decay rate was also high at this temperature. As temperature was increased from 35° to 60° C., glucose productivity increased fourfold (0.8 to 3 g/L/h) while the enzyme half-life decreased 30-fold ($2 \times 10^3$ to 70). These results indicate that low temperature operation greatly prolongs the life of the immobilized enzyme without sacrificing much in reaction rate. The choice of most profitable operating temperature will depend on the following: the required production rate based on demand, the amount of capital available for investment in reactor volume, the length of downtime, and the expense of recharging the reactor with fresh enzyme.

Variation of Enzyme Activity and Stability with pH. Starch-g-PAN immobilized glucoamylase was active over a relatively broad pH range (3.0–6.0) with maximum glucose productivity and minimum enzyme decay occurring about pH 4. The location and breadth of the activity optimum may depend on the specific carrier because of its influence on the microenvironment surrounding the enzyme.

*Variation on Enzyme Activity and Stability with Starch Content of the Carrier. By decreasing the extent of hydrolysis in 0.5N HCl, a series of carriers with increasing starch content was prepared from 28% add-on starch-g-PAN. FTIR analysis was used to quantitate starch content, and its dependence on the amount of heating during hydrolysis is shown in Table II.

TABLE II

| Starch-g-PAN Hydrolysis Conditions 0.5 N HCl | Resulting Carrier Composition[a] | |
|---|---|---|
| | Starch (%) | PAN (%) |
| HCl exposure, no heating | 72[b] | 28[b] |
| Heated to reflux | 30.9 | 69.1 |
| 2-min reflux | 23.9 | 76.1 |
| 15-min reflux | 7.1 | 92.9 |
| 90-min reflux | 2 | 98[c] |

[a]Except where indicated, carrier compositions were calculated from Fourier transform infrared spectra standardized against low molecular weight starch and a commercial polyacrylonitrile (PAN) preparation.
[b]From weight gain after graft polymerization.
[c]Residual carbohydrate shows lactone carbonyl in IR.

The activities and stabilities of the resulting enzyme-carrier adducts are illustrated in FIG. 1. It appears that brief (about 2-minutes) refluxing is optimum for binding active enzyme ($DG_o/C = 2.64$ g/g carrier/h), but heating to reflux and immediate cooling is optimum for maintaining reactor stability ($t_{\frac{1}{2}} = 1800$ h). These results suggest that both the PAN and the residual starch attached to it participate in enzyme binding and activity maintenance. This data indicate that a combination of factors leads to successful enzyme binding to the hydrolyzed polysaccharide graft copolymer, i.e., the glucoamylase's affinity for starch, the starch's affinity for water, and the starch's role as a spacer between PAN chains. All of these factors counteract the hydrophobic or water-repellent character of the PAN, making it more amenable to contact with aqueous enzyme or substrate. As shown in FIG. 1, glucose productivity per gram of carrier starch increases continuously as carrier starch content decreases. This suggests that only a limited amount of the available starch can participate in binding enzyme and that the presence of starch in the polymer carrier is only one of the many factors important for binding of the enzyme to the copolymer.

The diminshed enzyme activity and stability observed for the unhydrolyzed carrier indicates that removal of at least a portion of the starch from the starch-g-PAN granules is necessary to bind enzyme. It is theorized that this gives the copolymer granules sufficient porosity to allow for penetration by enzyme macromolecules during the contacting step. We found that digesting starch-g-PAN for about about 16 hours in glucoamylase at 50° C. gave essentially the same results as heating it under reflux in 0.5N HCl, thus making a separate acid hydrolysis step unnecessary. Other reagents that were substituted for HCl to catalyze starch hydrolysis to obtain active copolymer-enzyme products included periodate-alkali, perchloric acid in acetic acid, and trifluoroacetic acid.

Importance of Structure and Morphology. Although reported to bind protein, PAN homopolymer did not show activity after it was contacted with glucoamylase, washed, and suspended in either a batch or continuous reactor. Nor was activity observed when PAN was prepared via glucose-Ce(IV) rather than starch-Ce(IV) free radical initiation.

TABLE III

| PAN Treatment | Initial Glucose Productivity, DG (g/L/h) | Enzyme Activity Decay Rate Constant, $k_d$ ($h^{-1}$) |
|---|---|---|
| Starch-g-PAN with 28% add-on, 90-min 0.5 N HCl hydrolysis | 3.37 | 0.0032 |
| PAN homopolymer[a] | 0 | undefined |
| PAN formed by glucose-Ce (IV) free radical initiation[a] | 0 | undefined |
| PAN homopolymer precipitated from DMF prior to enzyme contacting[a] | 0.43 | 0.0058 |
| PAN homopolymer precipitated from DMSO prior to enzyme contacting[a] | 0.24 | 0.0054 |
| Starch-g-PAN (28% add-on, hydrolyzed 90 min in 0.5 N HCl) precipitated from DMF prior to enzyme contacting | 1.15 | 0.0036 |

[a]Not in accordance with the invention; used for comparison purposes.

However, by precipitating a dimethylformamide (DMF) or dimethylsulfoxide (DMSO) solution of PAN homopolymer in water prior to contacting with the enzyme, a measurable amount of active enzyme was bound, as shown in Table III. Furthermore, DMF-dissolved starch-g-PAN and DMF-dissolved PAN homopolymer exhibited similar enzyme activities after contacting and washing.

The granule structure of acid-hydrolyzed starch-g-PAN makes a significant contribution to the binding ability of these polymers, since activity is reduced by about a factor of two when granules are dissolved in DMF and then precipitated in water. Glucose-Ce(IV)-initiated polymerization apparently produces a tightly associated PAN structure that is resistant to aqueous penetration, which suggests that small glucose molecules cannot serve as spacers between PAN chains as do large starch molecules. PAN, when prepared by conventional methods, is hydrophobic, densely packed, and resistant to penetration by aqueous solutions of enzyme or carbohydrate. However, solution of PAN in DMF or DMSO followed by precipitation in water apparently renders the precipitated PAN particles more porous and thus more vulnerable to penetration and binding by enzyme and substrate.

Scanning electron micrographs indicate that particles size (and thus total surface area) is not the controlling factor that determines how readily PAN particles bind enzyme. Particles of PAN homopolymer and PAN prepared via glucose-Ce(IV) were 1–3 microns but had no enzyme-binding activity. In contrast, particles of PAN homopolymer precipitated from DMF and acid-hydrolyzed starch-g-PAN were much larger at 100 and 10 microns, respectively, yet they showed significant binding of the glucoamylase.

Relationship Between Percent PAN Add-on and Enzyme Activity. Starch-g-PAN was also prepared with 56 and 12% add-on in addition to the standard 28% (Table I). After HCl hydrolysis, enzyme contacting, and washing processes, both 12 and 56% add-on carriers exhibited enzyme activities ($DG_o$) lower than that of the graft copolymer containing 28% PAN (Table IV). Glucose productivity per g of PAN was about the same for 12 and 28% PAN add-on, but was much lower for the 56% add-on product. All three preparations showed about the same enzyme decay rate.

Application of Other Polysaccharide Copolymers as Glucoamylase Carriers. Cellulose-g-PAN, starch-g-polystyrene, and starch-gpoly(methyl methacrylate) were also evaluated (Table VI). Enzyme-carrier adducts from these copolymers possessed enzyme activities of varying strength and stability.

TABLE V

| Starch Type[a] | Granule Size (m) | Initial Glucose Productivity, $DG_o$ (g/L/h) | Enzyme Activity Decay Rate Constant, $k_d$ ($h^{-1}$) |
|---|---|---|---|
| Rice | 3–8 (Av. 5) | 1.22 | 0.0035 |
| Corn | 5–26 (Av. 15) | 3.34 | 0.0036 |
| Potato | ~40–110[b] | 0.69 | 0.0042 |

[a]For all cases, 28% add-on starch-g-PAN was prepared and tested according to standard procedure.
[b]Estimated from scanning electron micrographs.

TABLE VI

| Copolymer[a,b] | Initial Glucose Productivity, $DG_o$ (g/L/h) | Activity Decay Rate Constant, $k_d$ ($h^{-1}$) |
|---|---|---|
| Starch-g-PAN (28% Add-on) | 3.37 | 0.0032 |
| Cellulose-g-PAN (27.2% Add-on) | 1.03 | 0.0039 |
| Starch-g-PMMA (33.3% Add-on) | 0.13 | 11.5000 |
| Starch-g-PS (27% Add-on) | 0.28 | 0.0100 |

[a]Abbreviations: PAN = polyacrylonitrile, PMMA = poly(methylmethacrylate).

TABLE IV

| PAN Add-on (%) | Initial Glucose Productivity, $DG_o$ (g/L/h) | Specific Glucose Productivity, $DG_o/P$ (g/g PAN/h) | Enzyme Activity Decay Rate Constant, $k_d$ ($h^{-1}$) |
|---|---|---|---|
| 12 | 0.85 | 0.28 | 0.0028 |
| 28 | 2.21 | 0.32 | 0.0038 |
| 56 | 0.91 | 0.06 | 0.0027 |

Compared to the 28% add-on, the decrease in productivity $DG_o$ of the carrier prepared from 12% add-on starch-g-PAN is nearly proportional to the decrease in the amount of PAN per volume of reactor. However, this relationship between productivity and PAN concentration in the reactor breaks down for the high PAN add-on carrier. During the grafting process, the interstices of starch granules become filled with PAN as the polymerization proceeds, and the higher the precent add-on, the higher is the concentration of PAN, both on the surface and within the starch granule. It is theorized that PAN granules remaining after hydrolysis of high add-on (56%) starch-g-PAN have lesser permeability that lower add-on granules and permit lesser penetration by either aqueous enzyme or substrate, thus accounting for their low activity.

Variation of Enzyme Activity and Stability with Carrier Starch Type. Rice and potato starches were also used to prepare starch-g-PAN, and the resulting graft copolymers (see Table I) were then hydrolyzed and treated with enzyme as described for corn starch-g-PAN. Significant differences in bound enzyme activity were evident but all three carriers appeared about equal in terms of catalyst stability (Table V).

The most prominent difference among the three starch varieties is granule size (Table V), although subtle variations in chemical composition also exist. As can be seen from the data in Table V, the size (and therefore surface area) of the granule is not the deciding factor with regards to enzyme activity and stability.

PS = polystyrene.
[b]Once prepared all copolymers were hydrolyzed, enzyme contacted, washed, and evaluated according to standard procedure.

EXAMPLE 2

This example describes immobilization of α-amylase on hydrolyzed starch-g-PAN and repetitive batch reactions of immobilized α-amylase with dextrin.

Hydrolysis and Contacting with α-Amylase. A slurry of 5.0 g of starch-g-PAN (containing 29% PAN) in 100 ml of water containing 8 mg of calcium acetate and 5.0 g of commercial α-amylase solution ("Takatherm," Miles Laboratories, Inc.) was a prepared and the pH adjusted to 7.0 with 0.1N NaOH. The mixture was heated to 50° C., stirred at 90° C. for 30 minutes and then cooled to room temperature. The resulting hydrolyzed starch-g-PAN-enzyme product was separated by filtration, washed five times with water and stored as a wet filter cake (yield was about 9 g).

Repetitive Batch Reactions of Immobilized α-Amylase with Dextrin. A mixture of 6 g of wet PAN granules, 10.0 of a commercial starch dextrin (Clinton Company 277-B), and 150 ml of water was prepared and the pH was adjusted to 7.0 with 0.1N NaOH. The mixture was heated to 90° C., stirred at 90° C. for 30 minutes and then cooled to room temperature. The solid was separated by filtration, added to a fresh slurry of starch dextrin, and the same heating and cooling cycle was again carried out. PAN granules were recycled a total of four times with fresh slurries of dextrin, and each filtrate was freeze dried. Intrinsic viscosities on freeze dried solids were obtained in 90:10 (vol) dimethylsulfoxide-water and were used as a measure of starch hydrolysis and the amount of activity remaining in the immobilized α-amylase. For example, low intrinsic viscosities indicate a low starch molecular weight and thus a high degree of enzyme activity.

Table VII compares intrinsic viscosities for dextrin after reaction with PAN-immobilized α-amylase to intrinsic viscosity for an unreacted dextrin control. The low values of intrinsic viscosities observed relative to the control indicate that significant enzyme activity was retained by the enzyme immobilized on the copolymer granules. After the third and fourth applications of immobilized enzyme to a fresh dextrin sample, intrinsic viscosity began to increase, suggesting a gradual loss of activity due either to deactivation or leakage from the carrier

TABLE VII

| Number of Successive Hydrolyses Performed on Fresh Samples of Dextrin | Intrinsic Viscosity of Hydrolyzed Starch |
|---|---|
| 1 | 0.06 |
| 2 | 0.08 |
| 3 | 0.21 |
| 4 | 0.22 |
| Control (no enzyme treatment) | 0.46 |

EXAMPLE 3

In the following example, the activity and stability of hydrolyzed starch-g-PAN-immobilized glucoamylase to convert the soluble starch, maltodextrin, was tested in a continuous reactor.

Immobilized Glucoamylase. The starch-g-PAN carrier was prepared according to the standard procedure except that it was heated only long enough for refluxing to begin. This brief hydrolysis resulted in a copolymer composition of approximately 30% starch and 70% PAN which provided rapid conversion and minimum enzyme decay. After contacting enzyme and copolymer, the immobilized glucoamylase was tested in a continuous reactor.

Continuous Reactor Testing. A reactor fed 30 g/L maltose was compared with one fed 30 g/L maltodextrin produced from waxy maize to have a dextrose equivalent of 1 (STAR-DRI 1, A. E. Staley Manufacturing Co.) in order to evaluate differences in enzyme activity and reversion product formation on the two substrates. Maltodextrin was chosen to represent immobilized enzyme performance on starch because it dissolves easily to form relatively low viscosity aqueous solutions at room temperature, facilitating continuous feeding to the reactor setup. Except for the maltodextrin feed, the continuous reactor setup and conditions were the same as described above.

Immobilized Enzyme Activity. The glucose productivities of immobilized glucoamylase fed maltose and maltodextrin were similar at 11.4 and 12.4 g/L/h, respectively, with negligible deactivation. In addition, complete conversion of both substrates to glucose was accomplished when slow enough feed rates were used. Thus the carrier did not appear to interfere with the access of maltodextrin to the immobilized enzyme.

Reversion Products. HPLC analyses standardized for glucose, maltose, maltotriose, and maltotetrose showed that only glucose was formed when either maltose or maltodextrin was the substrate. The lack of reversion products allows maximum glucose production from substrate.

It is understood that the foregoing detailed description is given merely by way of illustration and that modification and variations may be made within, without departing from the spirit and scope of the invention.

We claim:

1. A method for preparing a polysaccharide graft copolymer-enzyme product, which consists essentially of:
   (a) hydrolyzing a polysaccharide graft copolymer, prepared by reaction of a vinyl or acrylic monomer with a polysaccharide, to remove a portion of said polysaccharide in said polysaccharide graft copolymer and obtain a final polysaccharide content in said hydrolyzed polysaccharide graft copolymer of 2 to 70%; and
   (b) contacting said hydrolyzed polysaccharide graft copolymer with an enzyme for a time sufficient to bind the enzyme to the copolymer.

2. The method of claim 1 wherein said final polysaccharide content in said hydrolyzed polysaccharide graft copolymer is 15 to 40%.

3. The method of claim 1 wherein said polysaccharide in said polysaccharide graft copolymer is selected from the group consisting of starch, cellulose, and xylan.

4. The method of claim 1 wherein said vinyl or acrylic monomer used to prepare said polysaccharide graft copolymer is selected from the group consisting of acrylonitrile, methyl acrylate, methyl methacrylate, ethyl acrylate, butyl acrylate, and styrene.

5. The method of claim 1 wherein said enzyme is a polysaccharide-degrading enzyme.

6. The method of claim 5 wherein said polysaccharide-degrading enzyme is selected from the group consisting of α-amylase, β-amylase, glucoamylase, cellulase, and xylanase.

7. The method of claim 1 wherein said polysaccharide graft copolymer is starch graft polyacrylonitrile and said enzyme is glucoamylase.

8. A polysaccharide graft copolymer-enzyme product prepared in accordance with the method of claim 1.

9. A polysaccharide graft copolymer-enzyme product prepared in accordance with the method of claim 2.

10. A polysaccharide graft copolymer-enzyme product prepared in accordance with the method of claim 3.

11. A polysaccharide graft copolymer-enzyme product prepared in accordance with the method of claim 4.

12. A polysaccharide graft copolymer-enzyme product prepared in accordance with the method of claim 5.

13. A polysaccharide graft copolymer-enzyme product prepared in accordance with the method of claim 6.

14. A polysaccharide graft copolymer-enzyme product prepared in accordance with the method of claim 7.

* * * * *